US009995712B2

(12) United States Patent
Moulds

(10) Patent No.: US 9,995,712 B2
(45) Date of Patent: Jun. 12, 2018

(54) SEGMENTED LINEAR ION MOBILITY SPECTROMETER DRIVER

(71) Applicant: Micromass UK Limited, Wilmslow (GB)

(72) Inventor: Richard Barrington Moulds, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days. days.

(21) Appl. No.: 15/315,587

(22) PCT Filed: Jun. 10, 2015

(86) PCT No.: PCT/GB2015/051698
§ 371 (c)(1),
(2) Date: Dec. 1, 2016

(87) PCT Pub. No.: WO2015/189607
PCT Pub. Date: Dec. 17, 2015

(65) Prior Publication Data
US 2017/0199153 A1    Jul. 13, 2017

(30) Foreign Application Priority Data

Jun. 10, 2014   (EP) ..................................... 14171737
Jun. 10, 2014   (GB) .................................. 1410258.6

(51) Int. Cl.
*G01N 27/62* (2006.01)
*H01J 49/24* (2006.01)
*H01J 49/00* (2006.01)

(52) U.S. Cl.
CPC ........ *G01N 27/622* (2013.01); *H01J 49/0031* (2013.01)

(58) Field of Classification Search
CPC ............... G01N 27/622; G01N 27/624; G01N 30/7266; H01J 49/067; H01J 49/24; H01J 49/26; H01J 49/42; H01J 49/426
(Continued)

(56) References Cited

U.S. PATENT DOCUMENTS 4,625,112 A    11/1986  Yoshida
7,154,087 B2 * 12/2006  Giannantonio ...... G01N 27/622
                                                   250/282

(Continued)

OTHER PUBLICATIONS

Fan Xin-Ean et al., "*Transient Drafting Electric Field for ION Mobility Spectrometer*", Instrument Technique and Sensor, Issue 2, pp. 68-70, (2008).

*Primary Examiner* — David A Vanore
(74) *Attorney, Agent, or Firm* — Womble Bond Dickinson (US) LLP; Deborah M. Vernon; Heath T. Misley

(57) ABSTRACT

An ion mobility spectrometer or separator is disclosed comprises plural groups of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors; a drift region; a first device arranged and adapted to pulse a packet of ions into the drift region so that the ions are caused to separate temporally and assume one or more ion distributions; and a control system arranged and adapted: (i) to cause at least some of the independently controllable voltage supplies to supply volt- (Continued)

ages to at least two adjacent groups of electrodes so as to substantially continuously subject at least part or substantially the whole of the one or more ion distributions to a first non-zero voltage gradient or a first non-zero constant or linear electric field as the one or more ion distributions progress along the drift region; and (ii) to cause at least some of the independently controllable voltage supplies to supply voltages to groups of electrodes other than the at least two adjacent groups of electrodes to create, maintain or apply a second different voltage gradient or a second different electric field across one or more portions of the drift region which are distal from the one or more ion distributions.

12 Claims, 9 Drawing Sheets

(58) Field of Classification Search
USPC .................. 250/282, 281, 288, 290, 293
See application file for complete search history.

(56) References Cited

U.S. PATENT DOCUMENTS

| | | | |
|---|---|---|---|
| 7,378,650 B2 | 5/2008 | Hashimoto et al. | |
| 8,507,852 B2 | 8/2013 | Makarov | |
| 8,618,475 B2 | 12/2013 | Clemmer et al. | |
| 8,829,433 B2* | 9/2014 | Green | G01N 27/624 250/290 |
| 8,872,102 B2* | 10/2014 | Clemmer | G01N 27/622 250/281 |
| 9,082,604 B2 | 7/2015 | Verenchikov | |
| 9,410,927 B2 | 8/2016 | Bateman et al. | |
| 9,429,543 B2 | 8/2016 | Jiang et al. | |
| 9,552,969 B2 | 1/2017 | Giles et al. | |
| 9,552,974 B2 | 1/2017 | Green et al. | |
| 9,659,760 B2* | 5/2017 | Gordon | H01J 49/167 |
| 9,779,924 B2* | 10/2017 | Gordon | H01J 49/025 |
| 9,786,481 B2* | 10/2017 | Gordon | H01J 49/24 |
| 2013/0292562 A1 | 11/2013 | Clemmer et al. | |

* cited by examiner

SEGMENTED LINEAR ION MOBILITY SPECTROMETER DRIVER

CROSS-REFERENCE TO RELATED APPLICATION APPLICATIONS

This application represents the U.S. National Phase of International Application number PCT/GB2015/051698 entitled "Segmented Linear Ion Mobility Spectrometer Driver" filed 10 Jun. 2015, which claims priority from and the benefit of United Kingdom patent application No. 1410258.6 filed on 10 Jun. 2014 and European patent application No. 14171737.1 filed on 10 Jun. 2014. The entire contents of these applications are incorporated herein by reference.

FIELD OF THE PRESENT INVENTION

The present invention relates generally mass spectrometry and in particular to ion mobility spectrometers or separators, mass spectrometers, methods of separating ions according to their ion mobility and method of mass spectrometry. According to an embodiment an ion mobility spectrometer or separator is provided wherein analyte ions are separated according to their ion mobility by subjecting the analyte ions to a constant electric field in the presence of a static buffer gas.

BACKGROUND

It is known to pre-separate ions temporally according to their ion mobility using an ion mobility spectrometer or separator ("IMS") prior to mass analysing the ions using a mass analyser. The mass analyser is arranged to mass analyse sequential packets of ions which emerge from the ion mobility spectrometer or separator and wherein each packet of ions comprises ions having substantially the same ion mobility.

The known ion mobility spectrometer or separator comprises a plurality of ring electrodes and a constant electric field is maintained along the entire length of the ion mobility spectrometer or separator as the distribution of ions progresses along the length of the ion mobility spectrometer or separator. A pressurised static buffer gas is provided within the ion mobility spectrometer or separator.

Analyte ions are pulsed into the ion mobility spectrometer or separator and the ions are then accelerated axially by the electric field. The analyte ions experience repeated collisions with the buffer gas molecules as the ions travel axially along the length of the ion mobility spectrometer or separator.

The analyte ions reach a constant drift velocity in the drift direction after continuous accelerations and collisions. The constant electric field exerts a greater force on higher-charge ions whilst larger ions experience more collisions with the buffer gas. As a result, the analyte ions are separated according to their ion mobility. It will be understood that the mobility of an ion is a function of the collisional cross-section of the ion with the buffer gas and also the charge of the ion.

A particular problem with known ion mobility spectrometers or separators is that in order to achieve a relatively high degree of temporal separation (i.e. to achieve a relatively high degree of separation according to the mobility of the ions) it is necessary for the ion mobility spectrometer or separator to have a relatively long drift length. However, constructing an ion mobility spectrometer or separator having a relatively long drift length is problematic since it necessitates the use of relatively high voltages which must be applied to at least the initial stages of the ion mobility spectrometer or separator.

It will be understood that applying relatively high voltages to at least some sections of the ion mobility spectrometer or separator requires the provision of relatively expensive and complex high voltage circuitry which is problematic.

Another disadvantage of applying high voltages to sections of the ion mobility spectrometer or separator is that the high voltages are likely to cause discharge or arcing if grounded objects are located nearby. As a result, the use of high voltages with an ion mobility spectrometer or separator imposes significant design constraints and necessitates the use of relatively complex and expensive electronics.

A yet further problem with an ion mobility spectrometer or separator which utilises high voltages is that the power consumption can also be relatively high.

WO 2013/093513 (Micromass) discloses an ion mobility separation device comprising an ion guiding path that extends in a closed loop. A DC voltage gradient is maintained along at least a portion of the longitudinal axis of the ion guide.

US 2013/292562 (Clemmer) discloses an ion mobility spectrometer in which a drift tube is partitioned into plural drift tube segments. Voltage sources V1 and V2 are connected to pairs of segments, and are alternately switched on to alternately establish two different constant electric fields across pairs of drift tube segments.

It is desired to provide an improved ion mobility spectrometer or separator and an improved method of separating ions according to their ion mobility.

SUMMARY

According to an aspect there is provided an ion mobility spectrometer or separator comprising:

plural groups of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors;

a drift region;

a first device arranged and adapted to pulse a packet of ions into the drift region so that the ions are caused to separate temporally and assume one or more ion distributions; and a control system arranged and adapted:

(i) to cause at least some of the independently controllable voltage supplies to supply voltages to at least two adjacent groups of electrodes so as to substantially continuously subject at least part or substantially the whole of the one or more ion distributions to a first non-zero voltage gradient or a first non-zero constant or linear electric field as the one or more ion distributions progress along the drift region; and (ii) to cause at least some of the independently controllable voltage supplies to supply voltages to groups of electrodes other than the at least two adjacent groups of electrodes to create, maintain or apply a second different voltage gradient or a second different electric field across one or more portions of the drift region which are distal from the one or more ion distributions.

Conventional ion mobility spectrometers which maintain a constant electric field across the whole length of the ion mobility spectrometer do not maintain a different (e.g. zero) electric field across portions of the ion mobility spectrometer which are distal from the ion distribution as it progresses along the length of the ion mobility spectrometer.

The ion mobility spectrometer according to US 2013/0292562 (Clemmer) only supplies one voltage to alternate drift tube segments at a time, and does not supply voltages to two adjacent electrode groups to generate a continuous constant or linear electric field across the two adjacent electrode groups while maintaining a different electric field across other portions of the drift region.

Ion mobility spectrometers are known wherein one or more transient DC voltages are applied to the electrodes and the one or more transient DC voltages are then translated along the length of the ion mobility spectrometer. However, such known arrangements do not continuously subject the whole of the ion distribution to a constant electric field. Furthermore, the transient DC voltages which are periodically applied do not result in a constant or linear electric field.

According to an embodiment a method of driving multiple electrodes so that a travelling field can be efficiently formed is provided.

The embodiment relates to circuitry which can be configured so as to drive a relatively large number of electrodes with a relatively small number of active circuits whilst allowing a great deal of flexibility in the fields that the electrodes can produce.

Known methods either produce a relatively unconfigurable output or require a large number of active circuits. The embodiment addresses the problem of controlling a large number of electrodes by controlling the electrodes using a small number of active electronic components so as to produce a moving zone having a linear electric field down it or along the length of the moving zone.

For example, according to a conventional arrangement an ion mobility spectrometer may be provided which is approximately 100 cm long. Assuming that the electrodes were spaced every 2 mm then such an arrangement would require approximately 500 voltage drivers or independently controllable voltage supplies. By way of contrast, according to an embodiment nine groups of electrodes each comprising approximately 114 electrodes could be utilised, wherein each group of electrodes required just two drivers or independently controllable voltage supplies. Accordingly, just 18 voltage drivers or independently controllable voltage supplies in total would be required according to an embodiment in contrast with 500 voltage drivers or independently controllable voltage supplies according to a conventional arrangement.

The control system may be arranged and adapted to cause at least some of the independently controllable voltage supplies to supply voltages that vary as a function of time between a maximum voltage and a minimum voltage to the corresponding groups of electrodes.

The control system may be arranged and adapted to cause at least some of the independently controllable voltage supplies to supply voltages that vary as a function of time to the corresponding group of electrodes, wherein each of the at least some of the independently controllable voltage supplies varies the voltage supplied to the corresponding group of electrode with a phase shift with respect to adjacent groups of electrodes.

The ion distribution may comprise a minimum displacement $d_{min}$ and a maximum displacement $d_{max}$ and wherein the length of the ion distribution $d_{max}-d_{min}$ progressively increases with time.

According to an embodiment ions having the lowest ion mobility have the minimum displacement $d_{min}$ and wherein ions having the highest ion mobility have the maximum displacement $d_{max}$ at any point in time.

According to an embodiment the first electric field is selected from the group consisting of: (i) <5 V/cm; (ii) 5-10 V/cm; (iii) 10-15 V/cm; (iv) 15-20 V/cm; (v) 20-25 V/cm; (vi) 25-30 V/cm; (vii) 30-35 V/cm; (viii) 35-40 V/cm; (ix) 40-45 V/cm; (x) 45-50 V/cm; and (xi) >50 V/cm.

The first electric field may be maintained on average across a distance selected from the group consisting of: (i) <10 cm; (ii) 10-20 cm; (iii) 20-30 cm; (iv) 30-40 cm; (v) 40-50 cm; (vi) 50-60 cm; (vii) 60-70 cm; (viii) 70-80 cm; (ix) 80-90 cm; (x) 90-100 cm; and (xi) >100 cm.

The amplitude or strength of the second electric field may be greater than the amplitude or strength of the first electric field.

The ion mobility spectrometer or separator may comprise a drift tube.

The ion mobility spectrometer or separator may comprise a plurality of electrodes.

According to an embodiment at least some of the electrodes are interconnected by a series of resistors or other components so as to form one or more groups of interconnected electrodes.

The ion mobility spectrometer or separator may comprise a first independently controllable voltage supply and a second independently controllable voltage supply, wherein a plurality of the electrodes are interconnected and an interconnected electrode is connected to the first voltage supply and another interconnected electrode is connected to the second voltage supply so that, in use, a non-zero voltage gradient is maintained between the first and second voltage supplies.

The ion mobility spectrometer or separator may comprise a third independently controllable voltage supply and a fourth independently controllable voltage supply, wherein a plurality of the electrodes are interconnected and an interconnected electrode is connected to the third voltage supply and another interconnected electrode is connected to the fourth voltage supply so that, in use, a non-zero voltage gradient is maintained between the third and fourth voltage supplies.

The ion mobility spectrometer or separator may comprise a fifth independently controllable voltage supply and a sixth independently controllable voltage supply, wherein a plurality of the electrodes are interconnected and an interconnected electrode is connected to the fifth voltage supply and another interconnected electrode is connected to the sixth voltage supply so that, in use, a non-zero voltage gradient is maintained between the fifth and sixth voltage supplies.

According to the embodiment 4, 6, 8, 10, 12, 14, 16, 18, 20 or >20 independently controllable voltage supplies may be provided wherein a plurality of interconnected electrodes may be connected between adjacent or neighbouring voltage supplies.

According to an example there is provided a mass spectrometer comprising an ion mobility spectrometer or separator as described above.

According to an aspect there is provided a method of separating ions according to their ion mobility comprising:

providing plural groups of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors;

providing a drift region;

pulsing a packet of ions into the drift region so that the ions are caused to separate temporally and assume one or more ion distributions;

causing at least some of the independently controllable voltage supplies to supply voltages to at least two adjacent groups of electrodes so as to substantially continuously subject at least part or substantially the whole of the one or more ion distributions to a first non-zero voltage gradient or a first non-zero constant or linear electric field as the one or more ion distributions progress along the drift region; and causing at least some of the independently controllable voltage supplies to supply voltages to groups of electrodes other than the at least two adjacent groups of electrodes to create, maintain or apply a second different voltage gradient or a second different electric field across one or more portions of the drift region which are distal from the one or more ion distributions.

The method may further comprise causing at least some of the independently controllable voltage supplies to supply voltages that vary as a function of time between a maximum voltage and a minimum voltage to the corresponding groups of electrodes.

The method may further comprise causing at least some of the independently controllable voltage supplies to supply voltages that vary as a function of time to the corresponding group of electrodes, wherein each of the at least some of the independently controllable voltage supplies varies the voltage supplied to the corresponding group of electrode with a phase shift with respect to adjacent groups of electrodes.

According to another aspect there is provided a method of mass spectrometry comprising a method of separating ions according to their ion mobility as described above.

According to another aspect there is provided a method of efficiently driving a set of electrodes so as to form one or more areas with an approximately linear field which traverses spatially. The method may comprise combining multiple resistive dividers with programmable offsets and synchronised scanning so as to generate a constant field that travels spatially along an intended ion flight path.

According to another aspect there is provided an ion guide comprising:

a plurality of electrodes; and a control system arranged and adapted:

(i) at a first time t1 to supply one or more voltages to one or more active sections of the ion guide so as to maintain a first substantially linear positive or negative axial voltage gradient or a first constant or linear electric field across the one or more active sections and wherein at the first time t1 the ion guide also comprises one or more inactive sections located either upstream and/or downstream of the one or more active sections; and (ii) at a second later time t2 to activate one or more previously inactive sections of the ion guide and/or to deactivate one or more previously active sections of the ion guide.

It will be understood that conventional ion mobility spectrometers which maintain a constant electric field across the whole length of the ion mobility spectrometer do not have any inactive sections wherein at a later time either the inactive sections are either activated or wherein previously active sections are deactivated.

According to the embodiments an ion guide is provided which is capable of generating a constant electric field that substantially tracks a packet of ions along its length such that the packet of ions is always subjected to a locally constant electric field.

According to the embodiments an ion guide is provided wherein only a section of the ion guide which immediately surrounds or is adjacent the packet of ions generates a constant electric field. Other sections of the ion guide may be arranged to have a different electric field or no electric field.

A highly efficient circuit configuration may be utilised to drive a plurality of electrodes and to generate a locally constant electric field that tracks a packet of ions which has been introduced into the ion guide.

An ion mobility spectrometer may be provided that comprises an ion guide capable of generating a locally constant electric field and which tracks a packet of ions along its length.

An active section of the ion guide may comprise a section of the ion guide through which at least some ions are being transmitted. An active section of the ion guide may also comprise a section of the ion guide immediately adjacent a section of the ion guide through which at least some ions are being transmitted.

An inactive section of the ion guide may comprise a section of the ion guide wherein substantially no ions of interest are present within the section. An inactive section of the ion guide may also comprise a section of the ion guide wherein substantially all ions have exited the section. An inactive section of the ion guide may comprise a section of the ion guide wherein substantially all ions have yet to enter the section.

The control system may be arranged to activate one or more previously inactive sections of the ion guide by applying one or more voltages to electrodes in the section in order to raise or lower the potential of the electrodes in that section so that they create a contiguous linear field throughout that section and at least one other adjacent section.

The control system may be arranged to translate the first substantially linear positive or negative axial voltage gradient or the first constant or linear electric field axially along the length of the ion guide.

The plurality of electrodes may be arranged in groups and the control system may be arranged to translate the first substantially linear positive or negative axial voltage gradient or the first constant or linear electric field along the length of the ion guide by supplying voltages to each section sequentially.

According to another aspect there is provided an ion mobility spectrometer or separator comprising an ion guide as described above.

According to another aspect there is provided a mass spectrometer comprising an ion guide as described above or an ion mobility spectrometer or separator as described above.

According to an aspect there is provided a method of guiding ions comprising:

providing an ion guide comprising a plurality of electrodes;

supplying, at a first time t1, one or more voltages to one or more active sections of the ion guide so as to maintain a first substantially linear positive or negative axial voltage gradient or a first constant or linear electric field across the one or more active sections and wherein at the first time t1 the ion guide also comprises one or more inactive sections located either upstream and/or downstream of the one or more active sections; and activating at a second later time t2 one or more previously inactive sections of the ion guide and/or deactivating one or more previously active sections of the ion guide.

According to another aspect there is provided a method of separating ions according to their ion mobility comprising a method of guiding ions as described above.

According to another aspect there is provided a method of mass spectrometry comprising a method of guiding ions described above or a method of separating ions according to their ion mobility as described above.

According to an aspect an ion guide is provided which comprises a device arranged and adapted to maintain an axial voltage gradient across a plurality of electrodes and to translate the axial voltage gradient progressively along the length of the ion guide.

The axial voltage gradient may generate a constant electric field locally and as the axial voltage gradient is translated along the length of the ion guide, the constant electric field may be progressively shifted along the length of the ion guide.

The plurality of electrodes of the ion guide may be arranged into sections along the length of the ion guide and the device may be arranged to translate the axial voltage gradient by causing the axial voltage gradient to be supplied to each section sequentially.

When the axial voltage gradient is supplied to a section of electrodes of the ion guide, a constant electric field may be generated locally in the section. Thus, as the axial voltage gradient is sequentially supplied to each section, the constant electric field is progressively shifted section by section along the length of the ion guide.

The device may be arranged to translate the axial voltage gradient progressively along the length of the ion guide according to predetermined time intervals. By setting appropriate time intervals at which the axial voltage gradient is translated along the length of the ion guide, it is possible to generate a local constant electric field that follows the movement of a packet of ions inside the ion guide.

The device may be arranged to maintain the axial voltage gradient by causing different DC voltages to be supplied to the plurality of electrodes.

Ions may be radially confined within the ion mobility spectrometer or separator by applying opposite phases of an AC or RF voltage to adjacent electrodes so as to create a radial pseudo-potential barrier which acts to confine ions radially within the ion mobility spectrometer or separator.

The device may be arranged to maintain the axial voltage gradient across a section of electrodes by causing a first voltage to be supplied to first electrodes in the section and a second voltage that is lower than the first voltage to be supplied to second electrodes in the section. For accelerating positive ions, the first electrodes may be disposed at the upstream end of the section, while the second electrodes may be disposed at the downstream end of the section, such that a decreasing voltage gradient may be maintained within the section in the downstream direction.

The device may be arranged to cause the axial voltage gradient to be supplied to each section sequentially by causing a first voltage to be supplied to first electrodes in a first section and a second voltage that is lower than the first voltage to be supplied to second electrodes in the first section during a first interval, and causing the first voltage to be supplied to third electrodes in a second section and the second voltage to be supplied to fourth electrodes in the second section during a second interval.

The device may be arranged to reduce the voltage supplied to the first and second electrodes of the first section after the first interval.

According to an embodiment the voltage gradient may be translated along the length of the ion guide section by section at predetermined intervals. The intervals may be set such that the voltage gradient, and thus the electric field, follows the movement of a packet of ions as it travels downstream along the ion guide. Furthermore, as the packet of ions leaves a section, such that the ions no longer feel the effect of the electric field from that section, the voltages supplied to the electrode(s) of that section may be reduced.

According to an embodiment each section may comprise two, three, four, five, six, seven, eight, nine, ten or more electrodes connected in series, wherein each electrode in a series may be separated from the next electrode in the series by a resistor. By connecting a plurality of electrodes in a section in series and separating each electrode by a resistive divider, a voltage gradient may be maintained across the section by connecting the section to a single voltage source instead of connecting each electrode to a separate voltage source. Such an embodiment simplifies the circuitry by supplying only a maximum voltage to a section of electrodes and the voltage at each subsequent electrode in the section is reduced according to the resistance of the resistive divider. The ion guide may be lengthened by connecting more electrodes in series in each section.

According to an aspect there is provided an ion mobility spectrometer or separator comprising:

at least a first group of electrodes, a second group of electrodes and a third group of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors;

a drift region;

a first device arranged and adapted to pulse a packet of ions into the drift region so that the ions are caused to separate temporally and assume one or more ion distributions; and a control system arranged and adapted:

(i) to cause at least some of the independently controllable voltage to supply voltages which subject substantially continuously at least part or substantially the whole of the one or more ion distributions to a first non-zero voltage gradient or a first non-zero constant or linear electric field as the one or more ion distributions progress along the drift region; and (ii) to cause at least some of the independently controllable voltage supplies to supply voltages which create, maintain or apply a second different voltage gradient or a second different electric field across one or more portions of the drift region which are distal from the one or more ion distributions.

According to another aspect there is provided a method of separating ions according to their ion mobility comprising:

providing at least a first group of electrodes, a second group of electrodes and a third group of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors;

providing a drift region;

pulsing a packet of ions into the drift region so that the ions are caused to separate temporally and assume one or more ion distributions;

causing at least some of the independently controllable voltage supplies to supply voltages which subject substantially continuously at least part or substantially the whole of the one or more ion distributions to a first non-zero voltage gradient or a first non-zero constant or linear electric field as the one or more ion distributions progress along the drift region; and causing at least some of the independently controllable voltage supplies to supply voltages which create, maintain or apply a second different voltage gradient or a second different electric field across one or more portions of the drift region which are distal from the one or more ion distributions.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap;

(iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c)

the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments together with other arrangements given for illustrative purposes only will now be described, by way of example only, and with reference to the accompanying drawings in which.

DETAILED DESCRIPTION

A conventional ion mobility spectrometer will first be described with reference to FIG. 1.

Figure 1:
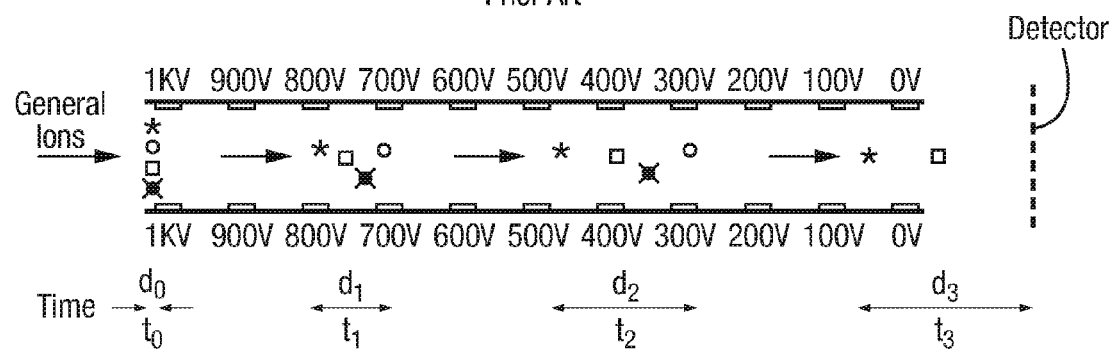
FIG. 1 shows a schematic diagram of a conventional ion mobility spectrometer.

FIG. 1 shows a conventional ion mobility spectrometer or separator comprising a drift tube. The drift tube comprises a plurality of ring electrodes wherein ions are caused to pass through an aperture formed by the ring electrodes.

A constant axial electric field is maintained along the whole of the axial length of the drift tube of the ion mobility spectrometer or separator. The electrodes may be distributed within a drift tube in a manner as shown in FIG. 1. The electrodes may be spaced away from the drift tube wall in order to reduce creepage problems and to reduce charging on insulating surfaces which might affect the ions.

The electrodes are individually connected to separate voltage sources so that a positive axial voltage gradient is maintained along the whole of the axial length of the ion mobility spectrometer or separator. An ion detector is provided downstream of the ion mobility spectrometer or separator and is arranged to detect ions which emerge from the exit of the ion mobility spectrometer or separator.

Ions separate due to the constant electric field giving a constant force but collisions with neutral gas molecules impedes the ions dependent upon their collisional cross section.

Figure 2:
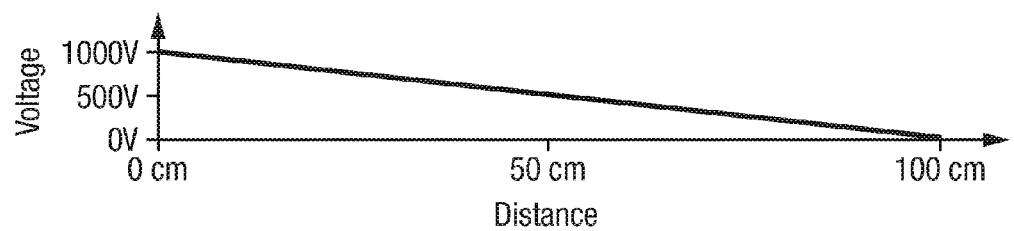
FIG. 2 shows the axial voltage profile maintained along the length of a conventional ion mobility spectrometer.

FIG. 2 shows a schematic of how the DC voltages which are applied to the electrodes progressively decrease along the axial length of the drift tube.

Figure 3:
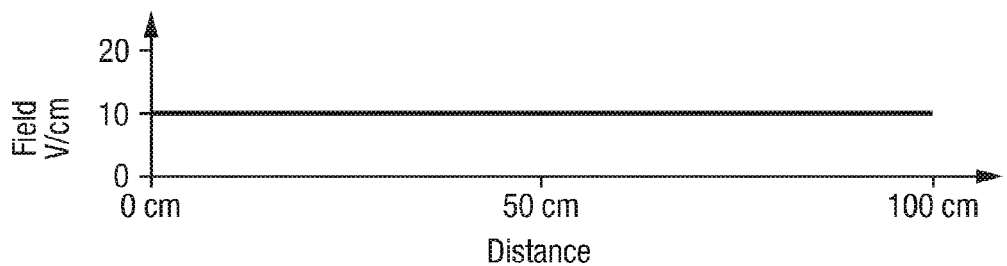
FIG. 3 shows the axial electric field profile maintained along the length of the conventional ion mobility spectrometer.

FIG. 3 shows how the axial DC voltage gradient as shown in FIG. 2 results in the establishment of a constant electric field along the whole length of the drift tube.

The constant electric field accelerates positively charged ions along and through the ion mobility spectrometer or separator towards the ion detector.

A packet of ions entering the ion mobility spectrometer or separator will gradually disperse as the packet of ions proceeds along the length of the drift tube towards the ion detector.

A packet of ions is shown in FIG. 1 having an initial dispersion $d_0$ at an initial time $t_0$ wherein $d_0$ is substantially zero. The packet of ions has a subsequent dispersion $d_1$ at a later time $t_1$, a greater dispersion $d_2$ at a subsequent time $t_2$ and a final dispersion $d_3$ at time $t_3$, wherein $d_3>d_2>d_1>d_0$. It is apparent that the packet of ions does not immediately disperse throughout the whole length of the ion mobility spectrometer or separator but gradually disperses reaching a maximum dispersion $d_3$ just prior to hitting or reaching the ion detector at the end of the drift tube.

In order to achieve a relatively large dispersal or dispersion it is necessary that the drift tube is relatively long. However, in order to generate a constant electric field along the entire length of a relatively long drift tube it will be apparent that a constant voltage gradient must be maintained along the whole length of the drift tube. Accordingly, for a long drift tube, large amplitude or high voltages must be developed, maintained or otherwise applied to the electrodes near the entrance region of the ion mobility spectrometer or separator in order to ensure that ions are efficiently separated according to their ion mobility.

The requirement of generating and distributing relatively high voltages for an extended period of time is disadvantageous in terms of energy consumption and requires high voltage electrical components which are relatively expensive.

Furthermore, applying relatively high voltages to the electrodes is also disadvantageous in that the application of high voltages can cause electrical discharge effects and/or arcing if grounded objects are located nearby. The use of high voltages therefore presents significant safety issues which requires relatively complex engineering solutions to overcome which increases the overall cost.

An embodiment will now be described with reference to FIG. 4. The embodiment is concerned with applying an electric field around a packet of ions and moving or translating the applied voltages down or along the length of the ion mobility spectrometer or separator thereby effectively tracking the ions so that the electric field seen by the ions remains substantially constant.

Figure 4:
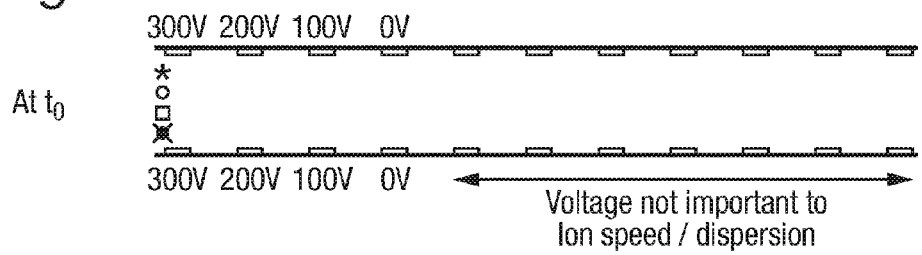
FIG. 4 shows a schematic diagram of an ion guide at an initial time $t_0$ according to an embodiment.

FIG. 4 shows an ion mobility separator or spectrometer according to an embodiment wherein a packet of ions is introduced into an ion guide at an initial time $t_0$. The ion guide may, for example, be disposed inside a drift tube of an ion mobility spectrometer or separator ("IMS"). An axial DC voltage gradient may be maintained across just some of the electrodes and the electrodes may be maintained at different DC potentials or voltages. The axial DC voltage gradient which is maintained across just some of the electrodes may then be translated progressively along the length of the ion guide in order to track the progress of the ions.

With reference to the particular embodiment shown in FIG. 4 a packet of ions is introduced into the ion guide at to and is subjected to an electric field generated when the first electrode is maintained at a DC potential of 300V, the second electrode is maintained at a DC potential of 200V, the third electrode is maintained at a DC potential of 100V and the fourth electrode is maintained at a DC potential of 0V. The fifth and subsequent electrodes may be maintained at 0V or another DC voltage.

Figure 5:
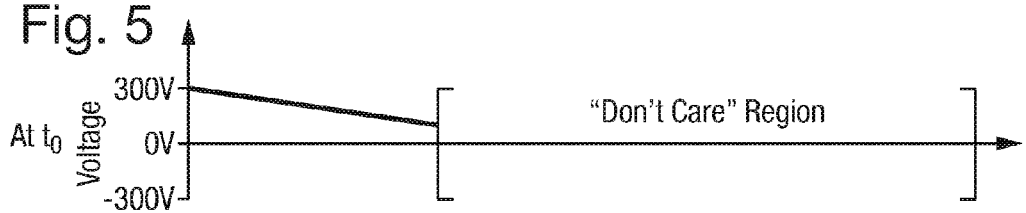
FIG. 5 shows the axial voltage profile maintained along the ion guide at initial time $t_0$ according to an embodiment.

FIG. 5 shows an axial DC voltage profile of the DC voltage gradient experienced by a packet of ions at an initial time $t_0$. The packet of ions experiences a decreasing axial voltage gradient across the first, second, third and fourth electrodes. The electrodes may be equally spaced axially and hence the axial DC voltage gradient results in a constant electric field across a first upstream section of the ion guide. At any given time, the packet of ions is accelerated by a force exerted upon it by the local electric field immediately surrounding the ions. The ions are therefore unaffected by the conditions in the far field.

In the example illustrated by FIGS. 4 and 5 the voltages of the electrodes in the region of the ion guide downstream of the fourth electrode do not significantly affect the acceleration of the packet of ions initially. Accordingly, the fifth and subsequent downstream electrodes may advantageously be kept at a different voltage without affecting the ions that are located within the first section.

As the ions travel along the axial length of the drift tube the ions will at a subsequent time $t_1$ enter a second section of the ion guide.

Figure 6:
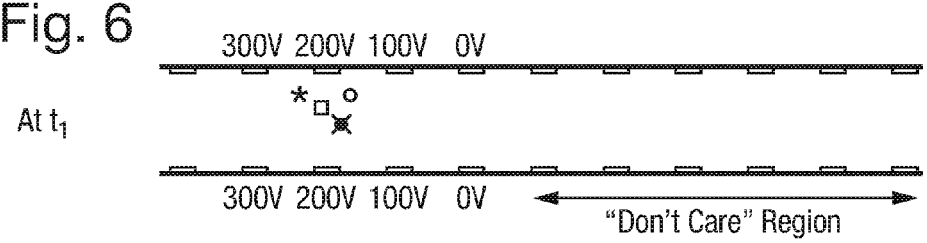
FIG. 6 shows a schematic diagram of the ion guide at a later time $t_1$ according to an embodiment.

FIG. 6 shows the ion mobility spectrometer or separator at time $t_1$ wherein the ions have begun to disperse and will now be influenced by the voltages applied to the second, third, fourth and fifth electrodes. The second electrode is maintained at a voltage of 300V, the third electrode is maintained at a voltage of 200V, the fourth electrode is maintained at a voltage of 100V and the fifth electrode is maintained at a voltage of 0V.

Figure 7:
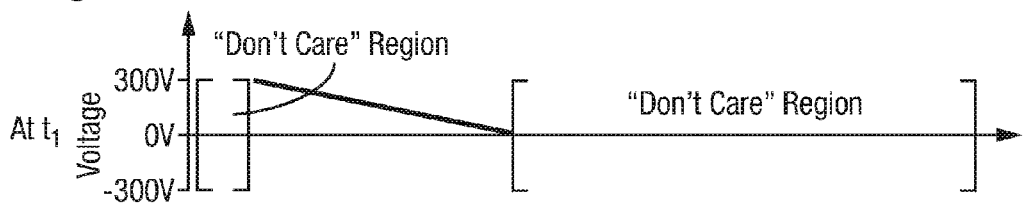
FIG. 7 shows the axial voltage profile maintained along the ion guide at time $t_1$ according to an embodiment.

FIG. 7 shows the axial DC voltage profile at the subsequent time t1 and highlights the axial voltage gradient which is maintained across the second section of the ion mobility spectrometer or separator.

It is apparent from FIG. 7 that the potentials of the first electrode and the sixth and subsequent electrodes do not have any significant impact upon the packet of ions.

It will be apparent that, from the point of view of the packet of ions, the electric field will appear constant since the far field effect of the voltages applied to the electrodes in the region of the ion guide upstream of the second electrode and downstream of the fifth electrode do not significantly affect the ions.

Figure 8:
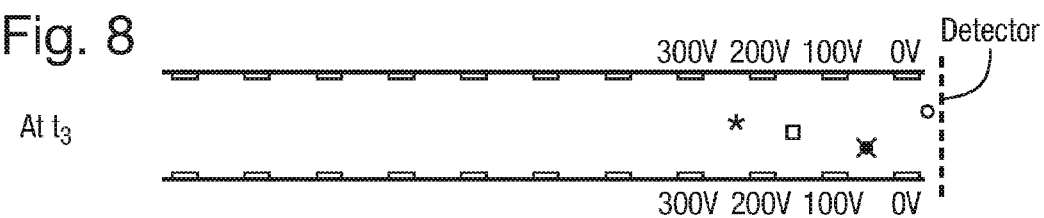
FIG. 8 shows a schematic diagram of the ion guide at a later time $t_3$ according to an embodiment.

FIG. 8 shows ions at a later time $t_3$ having entered a downstream section at the exit region of the ion guide immediately upstream of the ion detector. The eighth electrode is maintained at a voltage of 300V, the ninth electrode is maintained at a voltage of 200V, the tenth electrode is maintained at a voltage of 100V and the eleventh electrode is maintained at a voltage of 0V.

Figure 9:
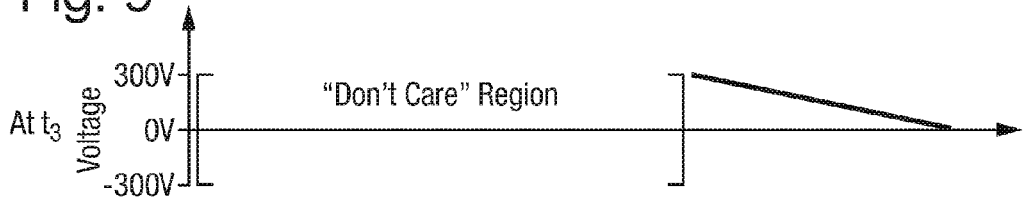
FIG. 9 shows the axial voltage profile maintained along the ion guide at time $t_3$ according to an embodiment.

FIG. 9 shows the axial voltage profile at time $t_3$ and illustrates how the ions again experience the same axial voltage gradient and hence experience effectively the same electric field as when the ion were transiting through upstream sections of the ion guide. Accordingly, the ions experience a constant or linear electric field as the ions progress through and long the length of the ion guide.

According to an embodiment a voltage supply may be provided and may be configured to supply voltages to the electrodes in the different sections of the ion guide. The electrodes may be arranged into one or more groups of electrodes, each group being interconnected by a series of resistors or other components so as to form a resistive divider. The voltage supply may furthermore be configured to effectively translate the axial DC voltage gradient along the length of the ion guide in synchronism with the passage of the ions through and along the length of the ion guide.

The voltage supply may comprise a control module for controlling voltage supplies to the electrodes. Driver circuitry may be provided which is configured to supply the desirable voltages to the electrodes. The control module may be configured to control the voltage supplies to each group of electrodes such that the voltage supplied to each group of electrodes varies as a function of time between a maximum voltage and a minimum voltage (which may be opposite in polarity). The voltage supplies for the groups of electrodes may be synchronised, for example by introducing a phase shift in the time-varying voltage supply of each adjacent group of electrodes, so as to continuously translate the constant or linear voltage gradient or electric field along the length of the ion guide.

According to the embodiment a moving voltage is effectively applied to the electrodes forming the ion mobility spectrometer or separator so as to form an approximation to a linear ramp.

Figure 10:
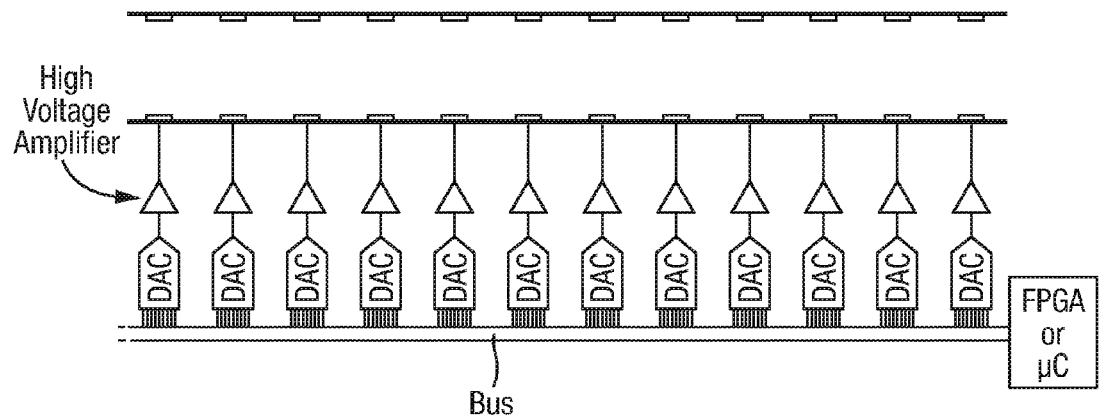
FIG. 10 shows an arrangement wherein the voltage supplied to each electrode is independently controllable.

FIG. 10 shows an arrangement wherein an ion guide is provided with a plurality of electrodes which are regularly spaced along the length of the ion guide. Each electrode is independently connected to a control module via a bus. The control module comprises a Field Programmable Gate Array ("FPGA") or a microcontroller.

A Digital to Analogue Convertor ("DAC") is connected to each electrode via a high voltage amplifier. The voltages supplied to each electrode are controlled such that, for example, a first DC voltage V1 is applied to a first electrode, a second voltage V2 is applied to a second electrode downstream of the first electrode, a third voltage V3 is applied to a third electrode downstream of the second electrode, and a fourth voltage V4 is applied to a fourth electrode downstream of the third electrode wherein V1>V2>V3>V4. Accordingly, a decreasing voltage gradient is maintained across a first section of the ion guide. Since each electrode is connected to the control module independently of each other, it is possible to independently control the voltage supplied to each individual electrode, thus enabling highly versatile control. However, utilising a large number of Digital to Analogue Converters results in a relatively complex and expensive circuit design.

Figure 11:
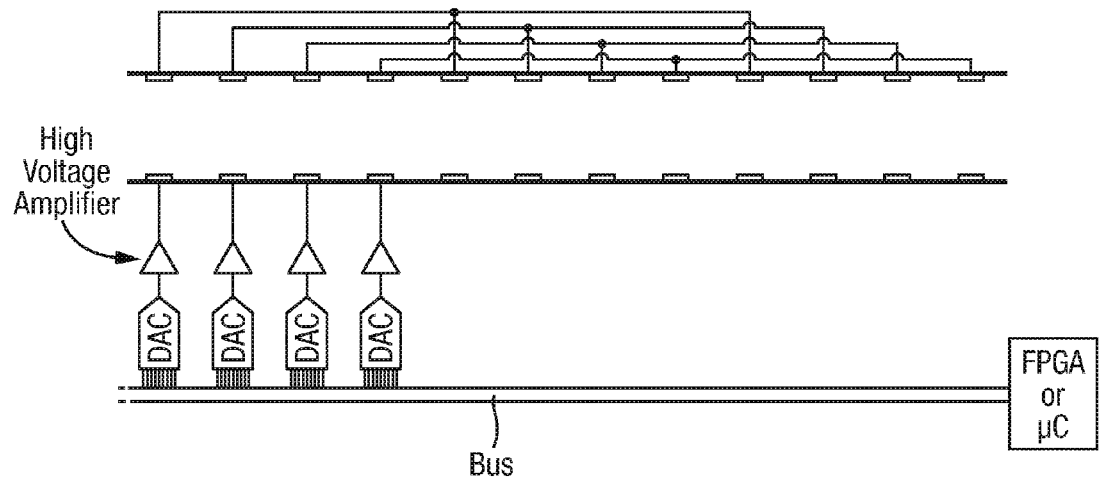
FIG. 11 shows another arrangement wherein every fourth electrode is interconnected thereby allowing a reduced number of independently controllable voltage supplies to be utilised.

FIG. 11 shows another arrangement similar to the arrangement described above with reference to FIG. 10 except that every fourth electrode is interconnected. More generally arrangements may be utilised wherein every (n)th electrode is interconnected. However, this only allows the ion packet to disperse over n/m of the length of the drift tube (where m is the total number of electrodes). This severely limits the usefulness of such a commoned electrode approach as relative drift times are often greater than 2. For example, if the relative mobility (effectively the ratio of the slowest to fastest species within an ion packet) within a group of ions is 3 then when the most mobile species reaches the end of the drift tube, the least mobile ion will only be $\frac{1}{3}^{rd}$ of the way down it. Clearly even commoning every $50^{th}$ electrode in a 100 electrode device would not be appropriate as 66% of the guide would need to be a contiguous constant field in order to fully separate the species, but only 50% could be made to have such a linear potential drop.

Figure 12:
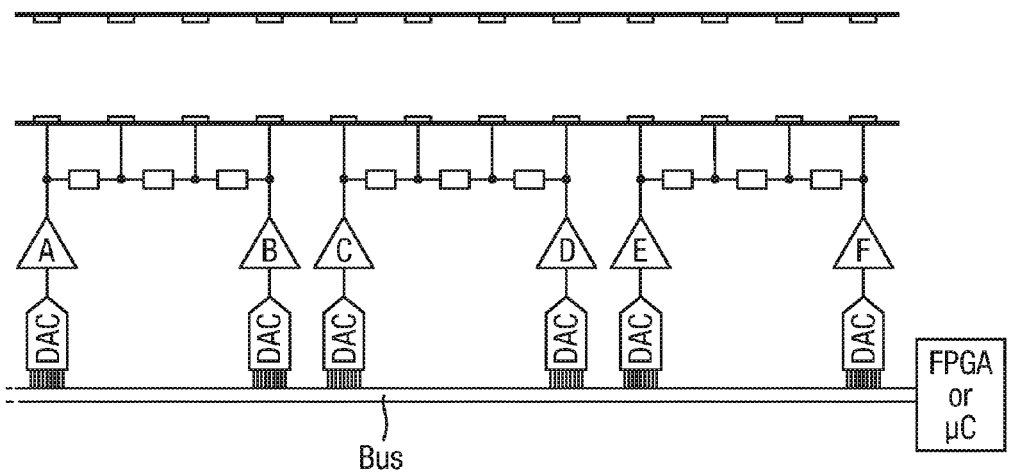
FIG. 12 shows an embodiment wherein the electrodes are divided into groups and wherein the electrodes in each group of electrodes are interconnected via resistors and wherein the voltage supplied to the first and last electrodes is independently controllable.

FIG. 12 illustrates an embodiment wherein electrodes are grouped into groups of three or more electrodes. The first and last (fourth) electrodes are each connected to high voltage amplifiers which are in turn connected to a respective Digital to Analogue Converter. Each Digital to Analogue Converter is in turn connected to a control module via a bus. The control module may comprise a Field Programmable Gate Array ("FPGA") or a microcontroller.

In the particular example shown in FIG. 12 each group of electrodes may comprise four electrodes which are each interconnected in series by individual resistors.

The first electrode in a first group of electrodes is driven by a high voltage amplifier connected to a first Digital to Analogue Converter A and the last (fourth) electrode in the first group of electrodes is driven by a high voltage amplifier connected to a second Digital to Analogue Converter B.

The first electrode in a second group of electrodes is driven by a high voltage amplifier connected to a third Digital to Analogue Converter C and the last (fourth) electrode in the second group of electrodes is driven by a high voltage amplifier connected to a fourth Digital to Analogue Converter D.

The first electrode in a third group of electrodes is driven by a high voltage amplifier connected to a fifth Digital to Analogue Converter E and the last (fourth) electrode in the third group of electrodes is driven by a high voltage amplifier connected to a sixth Digital to Analogue Converter F.

In use, when a voltage is supplied to a group of electrodes the voltage of the first electrode in the group may be at a maximum voltage and the respective voltage at each subsequent electrode may be lower than the maximum voltage by an amount determined by the resistance of the resistors which interlink the electrodes. Accordingly, by arranging the electrodes in groups along the length of the ion guide or ion mobility spectrometer or separator and providing a resistive divider between consecutive electrodes of each group, the voltage supply to a group of electrodes may be controlled and arranged to generate a voltage gradient across the group of electrodes.

According to the embodiment Digital to Analogue Converters and corresponding high voltage amplifiers are arranged in driver pairs and their outputs are connected to one another by a series of resistors. The resistors may be chosen so that the resistance between any two electrodes in any one chain is proportional to the distance between the electrodes. This enables a linear field to be generated along the flight path controlled by one driver pair.

As the ion packet spreads out and traverses the guide, the DACs can be driven so as to maintain a linear field along the flight path controlled by several pairs so as to encompass those ions. In an embodiment the electrodes are equidistant.

It will be apparent that the embodiment shown and described above with reference to FIG. 12 advantageously utilises a relatively simple circuit configuration that advantageously requires fewer expensive amplifiers and Digital to Analogue Convertors. Furthermore, the voltage control for generating and maintaining a voltage gradient across only a section of an ion guide is also simplified. The embodiment utilising resistive dividers coupled with a novel control method enables a desired waveform to be achieved at low cost and utilising a low complexity circuit design.

According to the embodiment if, for example, 100 steps are required in the dispersion region then only the number of resistors needs to be increased. The number of Digital to Analogue Converters and associated amplifiers only relates to the maximum voltage that the system can withstand reliably.

Figure 13:
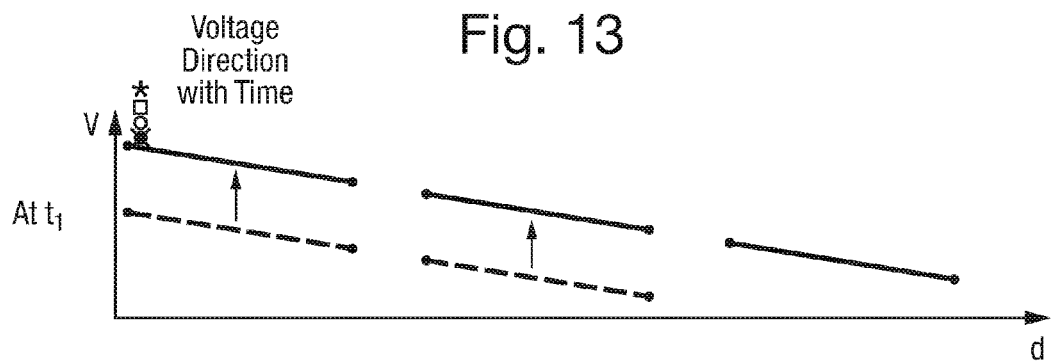
FIG. 13 illustrates an embodiment wherein first and second sections of an ion guide are activated at an initial time $t_1$.
Figure 14:
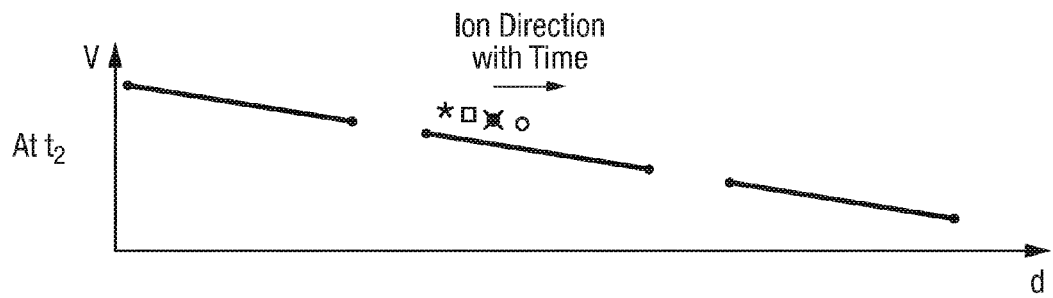
FIG. 14 shows the ion guide at a subsequent time $t_2$ wherein ions are separating according to their ion mobility in the second section of the ion guide.
Figure 15:
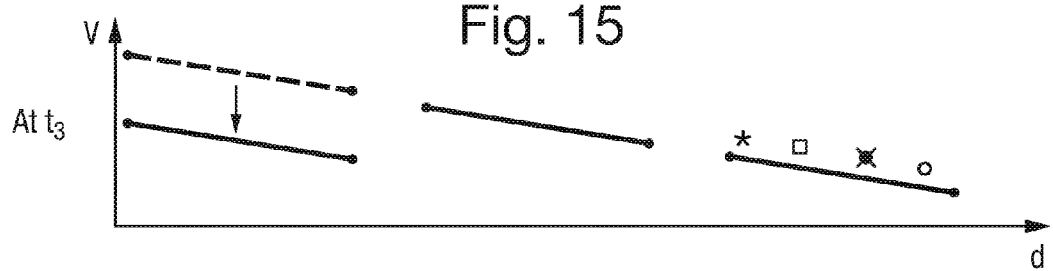
FIG. 15 shows the ion guide at a subsequent time $t_3$ wherein the first section of the ion guide is deactivated since all the ions are now present in the third section of the ion guide.

FIGS. 13-15 illustrate an embodiment wherein sections of an ion guide or ion mobility spectrometer or separator in close proximity to ions passing through the ion guide or ion mobility spectrometer or separator may be driven to separation voltages in advance of the ions either being pulsed into the ion mobility spectrometer or separator or in advance of the ions reaching the ion guide or ion mobility section.

FIG. 13 shows the first and second sections of an ion guide being driven at separation voltages from time t0 to time t1. It is apparent that the Digital to Analogue Convertors and associated amplifiers can be driven to give a constant field locally where the ions are injected. Increasing the voltages at amplifiers A, B, C, D with time causes the absolute voltage at the rear of the ion packet to remain substantially constant whilst keeping the ions on a constant gradient as they traverse the ion guide and separate according to their ion mobility.

FIG. 14 shows the ions at a subsequent time t2 wherein the ions are all present in the second section and have begun to disperse.

FIG. 15 shows the ions at a subsequent time t3 wherein the ions are all present in the third section and wherein the voltages applied to the first section may now be lowered since the voltages applied to the first section no longer has any significant influence upon the subsequent transit of the ions through the ion guide. According to the embodiment since the ions are no longer in the region controlled by amplifiers A, B then the voltages output by the amplifiers A, B can be reduced.

Where the ion packet (or at least the portion of that ion packet that is to be analysed) is predicted to be wholly absent from an area controlled by a driver pair, there is no longer a requirement for that pair to create a linear field in its flight path segment. The DACs can then be controlled so as to reduce their voltage output w.r.t. the surrounding metalwork (e.g. supporting structures and vacuum housing). This will reduce the likelihood of breakdown between those electrodes and the surrounding metalwork. However, setting the DACs directly to the chassis potential (typically ground potential) may cause a large voltage gradient to the adjacent electrodes driven by neighbouring driver pairs. If too high, breakdown there may occur or ions within the neighbouring flight path segment may be affected due to field penetration. Consequently the DACs should be programmed to minimise such problems (as exemplified in FIG. 16).

Figure 16:
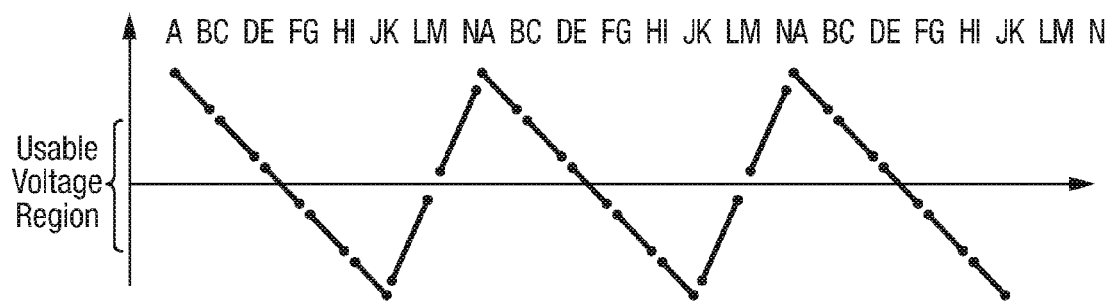
FIG. 16 shows a useable voltage region according to an embodiment.

FIG. 16 shows a useable voltage region. According to the embodiment shown in FIG. 16, 19 voltage driver pairs are arranged to separate ions in up to three regions. As ions progress from left to right the field surrounding them is maintained by increasing the voltage levels of the electrodes that surround them. However, if the voltage at A is at the supply's maximum, increasing the value at B would reduce the field between A and B. This means that the usable voltage range for creating moving linear fields is 100%× (N−2)/N of the supply range where N is the number of driver pairs allocated for a single mobility separation.

Figure 17:
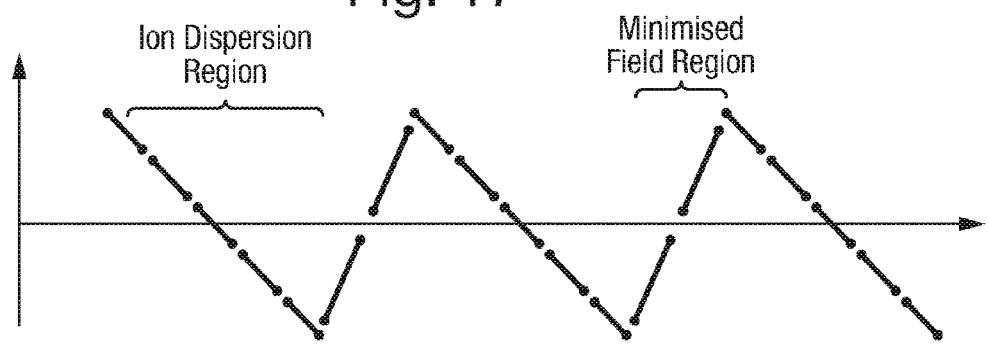
FIG. 17 shows an ion dispersion region and a minimised field region according to an embodiment.

FIG. 17 shows a corresponding ion dispersion region and a minimised field region. Here the supplies that are no longer being used for ion separation are programmed so as to reduce the absolute voltage on their electrodes without causing breakdown due to excessive field strength.

The "minimised field region" refers to the field w.r.t. surrounding metalwork (in this example the field in the local flight path region will be higher than that in the "ion dispersal region"). If the configuration is such that there are multiple regions that contain the linear dispersion field then the driver pairs in-between (JK, LM in FIG. 16) will best be programmed so as to form a linear reverse field between the ion dispersal regions. This will reduce the likelihood of breakdown in the minimised field region.

Although it is possible to drive every electrode in the ion mobility separation flight path with a unique DC potential with this method, it may not be necessary as the maximum dispersal length may be far shorter than the physical ion path length. Accordingly, in some cases the system complexity can be reduced by linking electrodes together For example, with reference to FIG. 16 the electrodes between A and B on the left may be linked to the electrodes between A and B in the middle and to the electrodes between A and B on the right. Electrodes between C and D, E and F etc. may also be linked in a similar manner. Such an embodiment further reduces the number of driver pairs and further simplifies wiring allowing for miniaturisation and/or cost reduction.

FIGS. 18A-L show an embodiment in which the ion guide comprises 10 driver pairs for 10 groups of electrodes, each group of electrodes being disposed over a distance of 10 cm, where a reference waveform is outputted by each driver pair to each group of electrodes according to the embodiment.

Figure 18A:
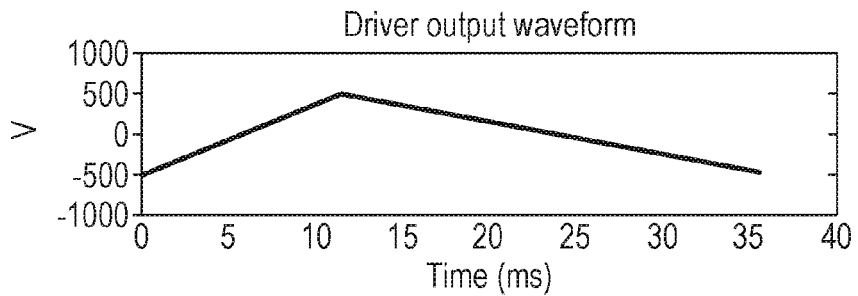
FIG. 18A shows an example of a reference driver output waveform used by voltage supplies to the electrodes according to an embodiment.

FIG. 18A shows the variation in the voltage supplied to each group of electrodes over a cycle of 36 ms. Each driver pair supplies a voltage to each group of electrodes that varies as a function of time between a minimum voltage of −500 V to a maximum voltage of +500 V.

Each group of electrodes is driven according to the reference driver output waveform, where the start time of a cycle for each group of electrodes is phase shifted with respect to the start time of the previous group of electrodes. The phase shift between each pair of adjacent groups of electrodes may be the same as the previous and/or subsequent pair, or it may be different.

The effect of introducing a phase shift between adjacent driver output is that the desired voltage gradient or constant/linear electric field, in this embodiment 20V/cm, propagates along the drift tube. In this embodiment, the linear electric field of 20V/cm traverses the drift tube over a period of 20 ms.

FIGS. 18B-L show a series of plots illustrating the variation in voltages (shown in solid lines) from each driver pair over the length of the drift tube and the resulting electric field (shown in dotted lines) over a period of 25 ms.

Figure 18B:
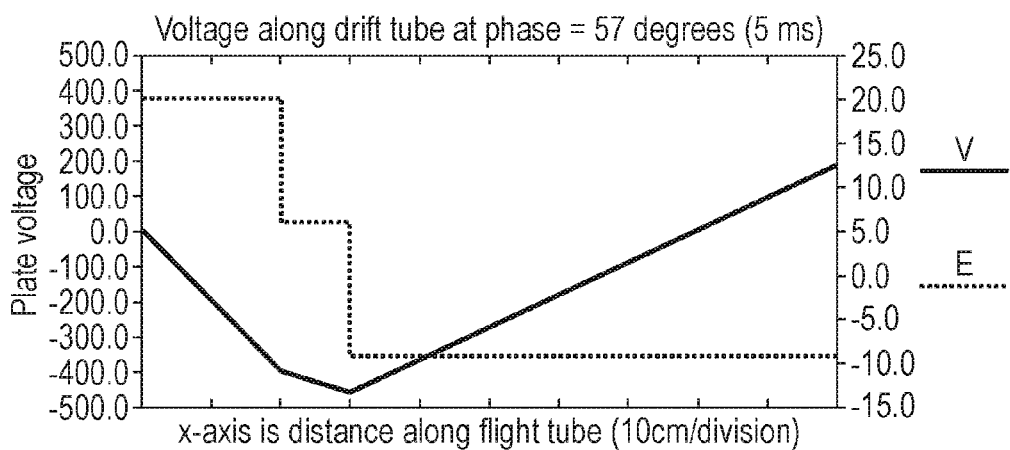
FIG. 18B shows the variation in voltages and electric field strength along the length of the ion guide at 5 ms.

FIG. 18B shows the variation in voltages (shown in solid lines) from each driver pair over the length of the drift tube and the resulting electric field (shown in dotted lines) at 5 ms.

Figure 18C:
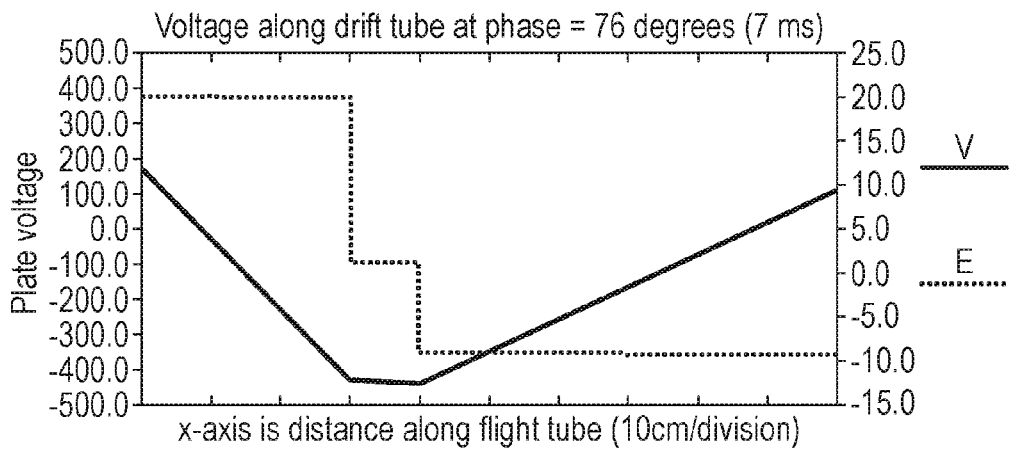
FIG. 18C shows the variation in voltages and electric field strength along the length of the ion guide at 7 ms.

FIG. 18C shows the variation in voltages (shown in solid lines) from each driver pair over the length of the drift tube and the resulting electric field (shown in dotted lines) at 7 ms.

Figure 18D:
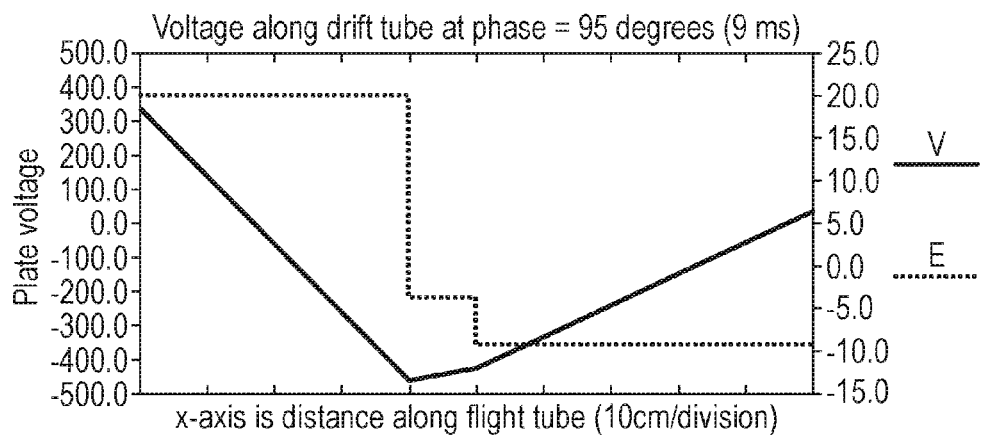
FIG. 18D shows the variation in voltages and electric field strength along the length of the ion guide at 9 ms.

FIG. 18D shows the variation in voltages (shown in solid lines) from each driver pair over the length of the drift tube and the resulting electric field (shown in dotted lines) at 9 ms.

Figure 18E:
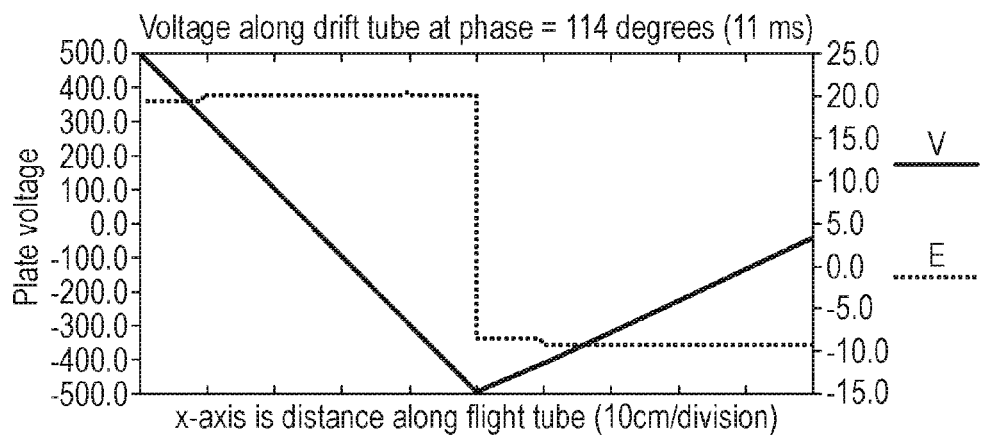
FIG. 18E shows the variation in voltages and electric field strength along the length of the ion guide at 11 ms.

FIG. 18E shows the variation in voltages (shown in solid lines) from each driver pair over the length of the drift tube and the resulting electric field (shown in dotted lines) at 11 ms.

Figure 18F:
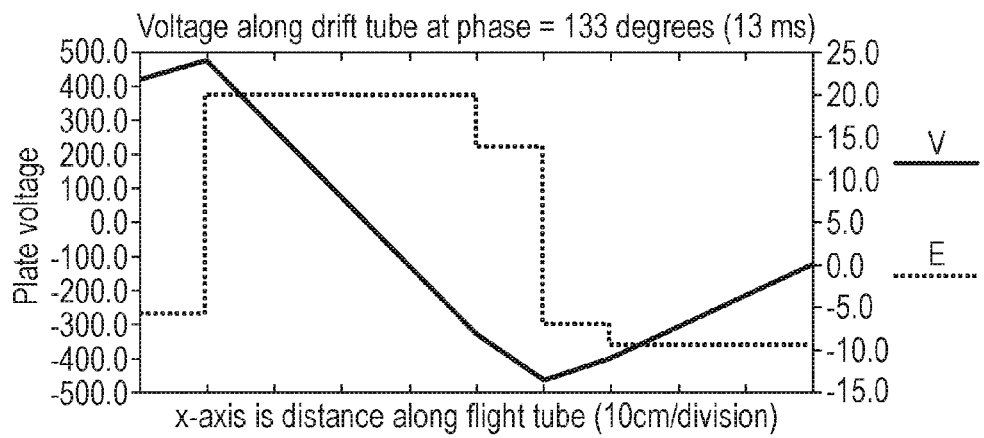
FIG. 18F shows the variation in voltages and electric field strength along the length of the ion guide at 13 ms.

FIG. 18F shows the variation in voltages (shown in solid lines) from each driver pair over the length of the drift tube and the resulting electric field (shown in dotted lines) at 13 ms.

Figure 18G:
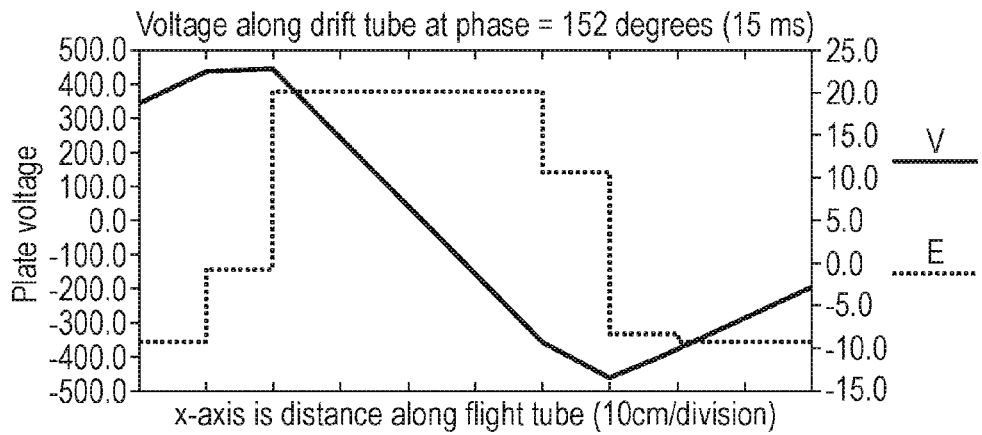
FIG. 18G shows the variation in voltages and electric field strength along the length of the ion guide at 15 ms.

FIG. 18G shows the variation in voltages (shown in solid lines) from each driver pair over the length of the drift tube and the resulting electric field (shown in dotted lines) at 15 ms.

Figure 18H:
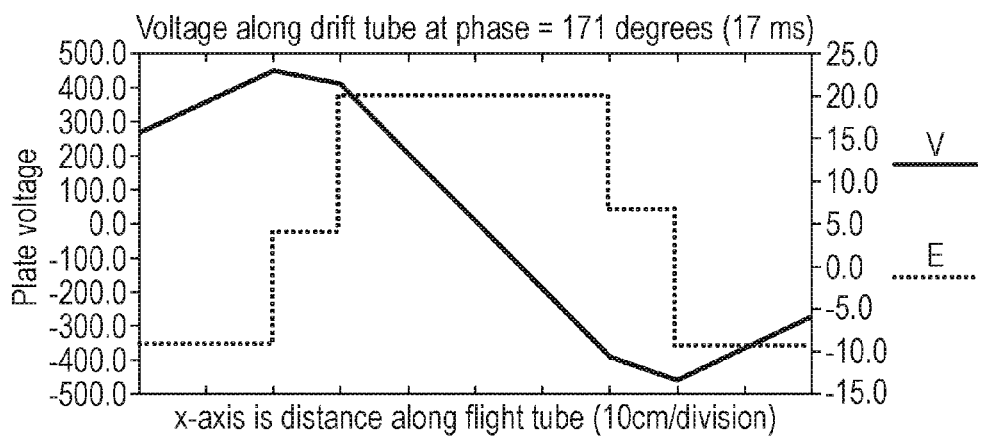
FIG. 18H shows the variation in voltages and electric field strength along the length of the ion guide at 17 ms.

FIG. 18H shows the variation in voltages (shown in solid lines) from each driver pair over the length of the drift tube and the resulting electric field (shown in dotted lines) at 17 ms.

Figure 18I:
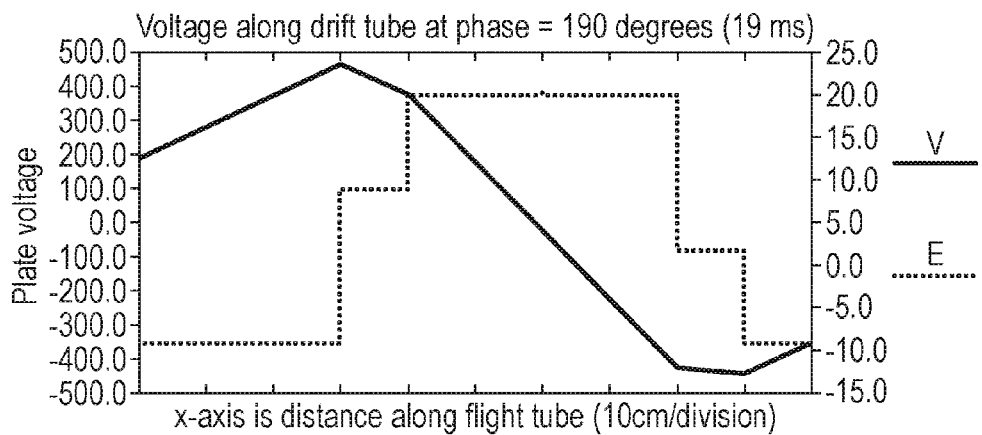
FIG. 18I shows the variation in voltages and electric field strength along the length of the ion guide at 19 ms.

FIG. 18I shows the variation in voltages (shown in solid lines) from each driver pair over the length of the drift tube and the resulting electric field (shown in dotted lines) at 19 ms.

Figure 18J:
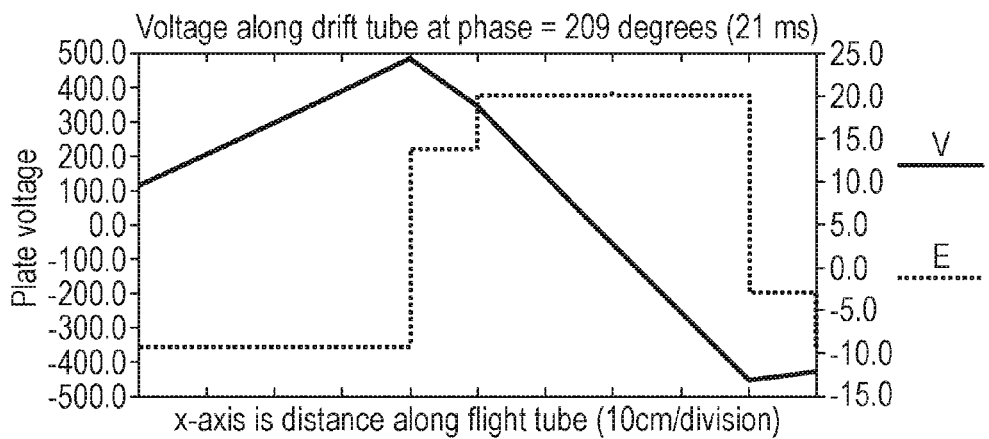
FIG. 18J shows the variation in voltages and electric field strength along the length of the ion guide at 21 ms.

FIG. 18J shows the variation in voltages (shown in solid lines) from each driver pair over the length of the drift tube and the resulting electric field (shown in dotted lines) at 21 ms.

Figure 18K:
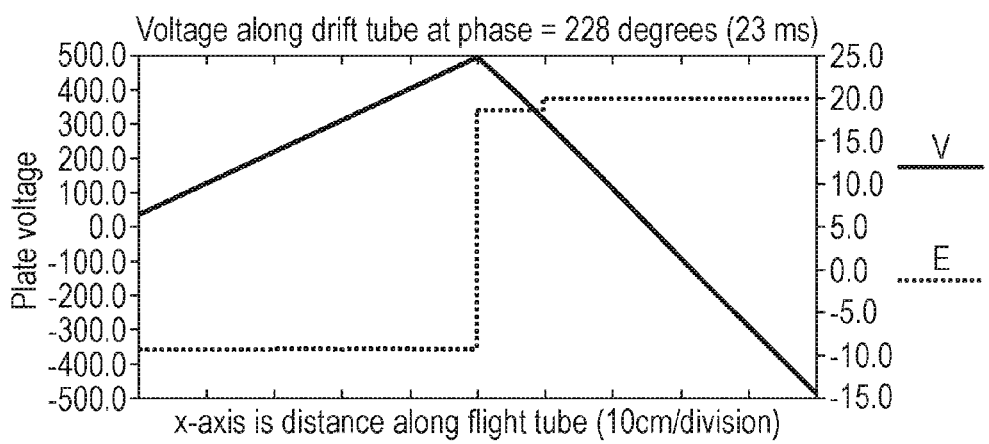
FIG. 18K shows the variation in voltages and electric field strength along the length of the ion guide at 23 ms and FIG. 18L shows the variation in voltages and electric field strength along the length of the ion guide at 25 ms.

FIG. 18K shows the variation in voltages (shown in solid lines) from each driver pair over the length of the drift tube and the resulting electric field (shown in dotted lines) at 23 ms.

Figure 18L:
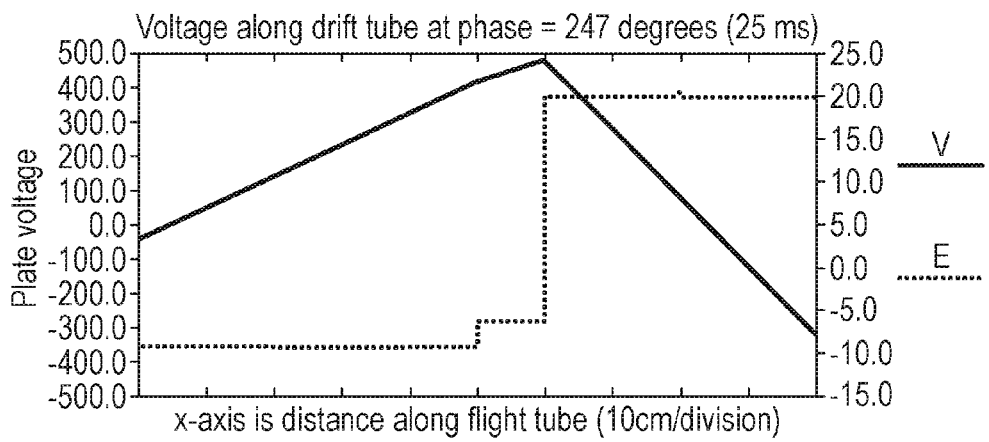

FIG. 18L shows the variation in voltages (shown in solid lines) from each driver pair over the length of the drift tube and the resulting electric field (shown in dotted lines) at 25 ms.

As can be seen from FIGS. 18B-L, the driver outputs can be configured with a phase shift such that a continuous linear electric field at the desired field strength of 20V/cm can be generated across at least two groups of electrodes at a time, and the time-varying driver output voltage causes the continuous linear electric field to propagate as ions progress along the drift tube and ensuring that part or all of the ions are subjected to the desired field strength, while maintaining the output voltage within the desired range of −500 V to +500 V.

According to further embodiments it is not essential that the ion mobility separation path or drift path be linear. For example, embodiments are contemplated wherein the ions may be directed to undertake zig-zag, circular, elliptical, helical, curved or non-linear paths.

According to an embodiment the constant electric field region which substantially tracks the ion distribution as the ion distribution progresses along the length of the ion mobility spectrometer may progress at either a linear or a non-linear rate. For example, since the ion dispersion will increase with time then embodiments are contemplated wherein the wavefront or progress of the electric field which tracks the ions may increase or progress in a non-linear manner.

According to an embodiment the areas behind and/or in front of the wavefront or progress of the electric field may be set to voltages which would cause any ions present to be ejected. Ejecting the ions is particularly useful in cyclic systems in order to reduce aliasing.

According to an embodiment the areas behind and/or in front of the wavefront or progress of the electric field may be set to voltages which would allow ions to pass through the area without dispersion. This arrangement may be useful when consecutive packets of ions are pulsed into the ion mobility spectrometer wherein it may be desirable to cause ion mobility separation in one packet of ions while allowing a subsequent packet of ions to pass through the drift region without separation.

According to a further embodiment the direction of separation may alternate. For example, according to an embodiment a low field may be applied and the voltages slowly progressed in a first direction and then a reverse high field may be applied for a short period of time in a second opposite direction and rapidly progressed in the second direction. According to this embodiment ions may be separated according to their differential ion mobility. Similarly, the first field could be the reverse high field and may be followed by a forward low field and then the sequence repeated.

Although the technology described herein has been described with reference to plural embodiments, it will be understood by those skilled in the art that various changes in form and detail may be made without departing from the scope as set forth in the accompanying claims.

The invention claimed is:

1. An ion mobility spectrometer or separator comprising:
plural groups of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors;
a drift region;
a first device arranged and adapted to pulse a packet of ions into the drift region so that the ions are caused to separate temporally and assume one or more ion distributions; and
a control system arranged and adapted:
(i) to cause at least some of the independently controllable voltage supplies to supply voltages to at least two adjacent groups of electrodes so as to substantially continuously subject at least part or substantially the whole of the one or more ion distributions to a first non-zero voltage gradient or a first non-zero constant or linear electric field as the one or more ion distributions progress along the drift region; and
(ii) to cause at least some of the independently controllable voltage supplies to supply voltages to groups of electrodes other than the at least two adjacent groups of electrodes to create, maintain or apply a second different voltage gradient or a second different electric field across one or more portions of the drift region which are distal from the one or more ion distributions.

2. An ion mobility spectrometer or separator as claimed in claim 1, wherein the control system is arranged and adapted to cause at least some of the independently controllable voltage supplies to supply voltages that vary as a function of time between a maximum voltage and a minimum voltage to the corresponding groups of electrodes.

3. An ion mobility spectrometer or separator as claimed in claim 1, wherein the control system is arranged and adapted to cause at least some of the independently controllable voltage supplies to supply voltages that vary as a function of time to the corresponding group of electrodes, wherein each of the at least some of the independently controllable voltage supplies varies the voltage supplied to the corresponding group of electrode with a phase shift with respect to adjacent groups of electrodes.

4. An ion mobility spectrometer or separator as claimed in claim 1, wherein the first device is arranged and adapted to pulse a packet of ions into the drift region to form an ion distribution comprising a minimum displacement $d_{min}$ and a maximum displacement $d_{max}$ and wherein the length of the ion distribution $d_{max}-d_{min}$ progressively increases with time.

5. An ion mobility spectrometer or separator as claimed in claim 4, wherein the first device is arranged and adapted to pulse a packet of ions into the drift region to form an ion distribution wherein ions having the lowest ion mobility have the minimum displacement $d_{min}$ and wherein ions having the highest ion mobility have the maximum displacement $d_{max}$ at any point in time.

6. An ion mobility spectrometer or separator as claimed in claim 1, wherein the control system is configured to cause the strength of the first electric field to be selected from the group consisting of: (i)<5 V/cm; (ii) 5-10 V/cm; (iii) 10-15 V/cm; (iv) 15-20 V/cm; (v) 20-25 V/cm; (vi) 25-30 V/cm; (vii) 30-35 V/cm; (viii) 35-40 V/cm; (ix) 40-45 V/cm; (x) 45-50 V/cm; and (xi) >50 V/cm.

7. An ion mobility spectrometer or separator as claimed in claim 1, wherein the control system is configured to cause the first electric field to be maintained on average across a distance selected from the group consisting of: (i)<10 cm; (ii) 10-20 cm; (iii) 20-30 cm; (iv) 30-40 cm; (v) 40-50 cm; (vi) 50-60 cm; (vii) 60-70 cm; (viii) 70-80 cm; (ix) 80-90 cm; (x) 90-100 cm; and (xi) >100 cm.

8. An ion mobility spectrometer or separator as claimed in claim 1, wherein the control system is configured to cause the second electric field to have an amplitude or strength greater than the amplitude or strength of the first electric field.

9. An ion mobility spectrometer or separator as claimed in claim 1, wherein the ion mobility spectrometer or separator comprises a drift tube.

10. A method of separating ions according to their ion mobility comprising:

providing plural groups of electrodes, each group of electrodes comprising: (i) a first electrode connected to a first independently controllable voltage supply; (ii) one or more intermediate electrodes; and (iii) a second electrode connected to a second independently controllable voltage supply, wherein the first electrode, the one or more intermediate electrodes and the second electrode are interconnected by a series of resistors or other components so as to form a resistive divider so that the potential of the one or more intermediate electrodes is determined by the voltages supplied by the first and second voltage supplies and the resistance of the resistors;

providing a drift region;

pulsing a packet of ions into the drift region so that the ions are caused to separate temporally and assume one or more ion distributions;

causing at least some of the independently controllable voltage supplies to supply voltages to at least two adjacent groups of electrodes so as to substantially continuously subject at least part or substantially the whole of the one or more ion distributions to a first non-zero voltage gradient or a first non-zero constant or linear electric field as the one or more ion distributions progress along the drift region; and causing at least some of the independently controllable voltage supplies to supply voltages to groups of electrodes other than the at least two adjacent groups of electrodes to create, maintain or apply a second different voltage gradient or a second different electric field across one or more portions of the drift region which are distal from the one or more ion distributions.

11. A method of separating ions as claimed in claim 10 comprising causing at least some of the independently controllable voltage supplies to supply voltages that vary as a function of time between a maximum voltage and a minimum voltage to the corresponding groups of electrodes.

12. A method of separating ions as claimed in claim 10 comprising causing at least some of the independently controllable voltage supplies to supply voltages that vary as a function of time to the corresponding group of electrodes, wherein each of the at least some of the independently controllable voltage supplies varies the voltage supplied to the corresponding group of electrode with a phase shift with respect to adjacent groups of electrodes.

* * * * *